United States Patent [19]
Hallenbach et al.

[11] Patent Number: 5,854,241
[45] Date of Patent: Dec. 29, 1998

[54] PYRIDO[3,2,1-I,J][3,1]BENZOXAZINE DERIVATIVES

[75] Inventors: Werner Hallenbach, Monheim; Thomas Himmler, Odenthal; Thomas Jaetsch, Köln; Burkhard Mielke, Leverkusen; Klaus Dieter Bremm, Recklinghausen; Rainer Endermann, Wuppertal; Franz Pirro, Langenfeld, all of Germany; Michael Stegemann, Shawnee Mission, Kans.; Heinz-Georg Wetzstein, Köln, Germany

[73] Assignee: Bayer Aktiengesellschaft, Leverkusen, Germany

[21] Appl. No.: 765,212
[22] PCT Filed: Jun. 28, 1995
[86] PCT No.: PCT/EP95/02510
 § 371 Date: Jan. 3, 1997
 § 102(e) Date: Jan. 3, 1997
[87] PCT Pub. No.: WO96/01829
 PCT Pub. Date: Jan. 25, 1996

[30] Foreign Application Priority Data

Jul. 11, 1994 [DE] Germany ............ 44 24 369.3

[51] Int. Cl.$^6$ .................. C07D 498/06; C07D 265/00; C07D 221/00; A61K 31/535
[52] U.S. Cl. .................. 514/230.2; 514/229.8; 544/58.5; 544/58.6; 544/101; 544/14; 544/54
[58] Field of Search .................. 544/97, 589, 90, 544/103, 54, 58.5, 101, 58.6, 32; 514/235.5, 230.2, 230.5, 229.8; 546/115, 126, 116

[56] References Cited

U.S. PATENT DOCUMENTS

| 3,055,894 | 9/1962 | Gerster | 260/247.5 |
|---|---|---|---|
| 3,551,565 | 12/1970 | Gerster | 424/248 |
| 3,883,522 | 5/1975 | Gerster | 260/244 |
| 3,966,743 | 6/1976 | Berger et al. | 260/287 CF |
| 3,984,548 | 10/1976 | Gerster | 424/248 |
| 4,382,892 | 5/1983 | Hayakawa et al. | 260/243.3 |
| 4,835,163 | 5/1989 | Verniere et al. | 514/312 |
| 5,096,901 | 3/1992 | Ward et al. | 514/214 |
| 5,362,734 | 11/1994 | Ward et al. | 514/294 |
| 5,583,135 | 12/1996 | Matsuo et al. | 514/230.2 |

FOREIGN PATENT DOCUMENTS

| 047005 | 3/1982 | European Pat. Off. . |
|---|---|---|
| 373531 | 6/1990 | European Pat. Off. . |

*Primary Examiner*—S. Mark Clardy
*Assistant Examiner*—Sabiha N. Qazi
*Attorney, Agent, or Firm*—Sprung Kramer Schaefer & Briscoe

[57] ABSTRACT

Disclosed are pyrido[3,2,1-i,j][3,1]benzoxazine compounds of the formula (I):

(I)

wherein z represents a radical having the formula:

wherein B represents —CH$_2$—, —O— or a direct bond; and the other variables in formula (I) and Z are as described herein. The compounds have antibacterial properties and also disclosed are antibacterial compositions containing them and methods of using them to prevent or combat bacterial infections. Methods for preparing the compounds are also disclosed.

7 Claims, No Drawings

PYRIDO[3,2,1-I,J][3,1]BENZOXAZINE DERIVATIVES

This application has been filed under 35 USC 371 as National Stage application of PCT/EP95/02510 filed Jun. 28, 1995.

The invention relates to new pyrido[3,2,1-i,j][3,1] benzoxazine derivatives, to processes for their preparation, and to antibacterial compositions comprising them.

It has already been disclosed that pyridobenzoxazinecarboxylic acids have an antibacterial activity. Examples can be found in EP-O 373 531.

There have now been found compounds of the general formula (I)

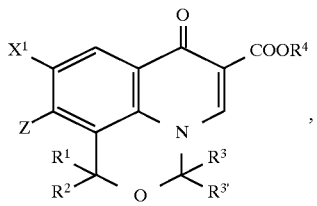

in which $R^1$ represents hydrogen or $C_1$–$C_4$-alkyl which is optionally substituted by hydroxyl or halogen, $R^2$ independently of $R^1$ represents hydrogen or methyl, $R^3$ represents hydrogen or $C_1$–$C_4$-alkyl, $R^{3'}$ independently of $R^3$ represents hydrogen or methyl, $R^4$ represents hydrogen, alkyl having 1 to 4 carbon atoms which is optionally substituted by hydroxyl, methoxy, amino, methylamino or dimethylamino, or represents (5-methyl-2-oxo-1,3-dioxol-4-yl)-methyl, $X^1$ represents hydrogen or halogen, Z represents radicals of the structures

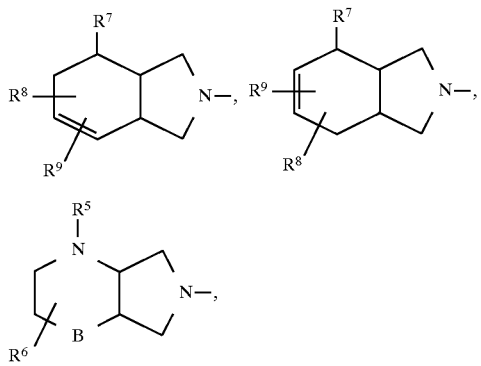

in which $R^7$ represents hydrogen, hydroxyl, —$NR^{10}R^{11}$, hydroxymethyl, —$CH_2$—$NR^{10}R^{11}$, carboxyl, methoxycarbonyl or ethoxycarbonyl, where $R^{10}$ represents hydrogen, $C_1$–$C_3$-alkyl which is optionally substituted by hydroxyl, or represents alkoxycarbonyl having 1 to 4 C atoms in the alkoxy moiety, or $C_1$–$C_3$-acyl, $R^{11}$ represents hydrogen or methyl, $R^8$ represents hydrogen, straight-chain or branched $C_1$–$C_3$-alkyl or cyclopropyl, $R^9$ represents hydrogen or methyl, $R^6$ represents hydrogen or methyl, $R^5$ represents hydrogen, methyl or radicals of the structures —CH=CH—$CO_2R^5$, —$CH_2$—$CH_2$—$CO_2R^{5'}$, —$CH_2$—CO—$CH_3$, —$CH_2$—$CH_2$—CN, $R^{5'}$ represents methyl or ethyl, and B represents —$CH_2$—, O or a direct bond.

The compounds of the formula (I) can exist in the form of racemates or enantiomerically pure compounds, in the form of their pharmaceutically utilizable hydrates and acid addition salts, and in the form of their alkali metal salts, alkaline earth metal salts, silver salts and guanidinium salts.

The compounds of the formula (I) are obtained when compounds of the formula (II)

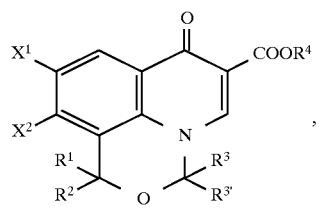

in which $R^1$, $R^2$, $R^3$, $R^{3'}$, $R^4$ and $X^1$ have the abovementioned meaning and $X^2$ represents halogen, in particular fluorine or chlorine, are reacted with compounds of the formula (III)

Z—H    (III)

in which

Z has the abovementioned meaning, if appropriate in the presence of acid scavengers.

Compared with known representatives of this structural type, the compounds according to the invention have a more powerful antibacterial action, in particular in the Gram-positive sector. They are therefore suitable as active compounds for human and veterinary medicine, veterinary medicine also including the treatment of fish for the therapy or the prevention of bacterial infections.

Preferred compounds of the formula (I) are those in which $R^1$ represents hydrogen or $C_1$–$C_3$-alkyl which is optionally substituted by hydroxyl, $R^2$ independently of $R^1$ represents hydrogen or methyl, $R^3$ represents hydrogen, methyl or ethyl, $R^{3'}$ independently of $R^3$ represents hydrogen or methyl, $R^4$ represents hydrogen, alkyl having 1 to 4 carbon atoms which is optionally substituted by hydroxyl, methoxy, amino, methylamino or dimethylamino, or represents (5-methyl-2-oxo-1,3-dioxol-4-yl)methyl, $X^1$ represents hydrogen, fluorine or chlorine, Z represents radicals of the structures

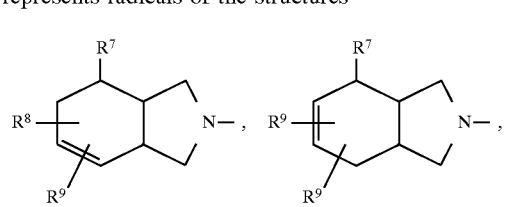

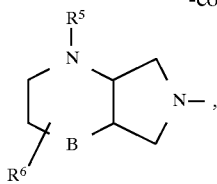

in which
- $R^7$ represents hydrogen, hydroxyl, $-NR^{10}R^{11}$, hydroxymethyl or $-CH_2-NR^{10}R^{11}$,
  where
  - $R^{10}$ represents hydrogen, $C_1-C_2$-alkyl which is optionally substituted by hydroxyl, or represents alkoxycarbonyl having 1 to 4 C atoms in the alkoxy moiety, or $C_1-C_3$-acyl,
  - $R^{11}$ represents hydrogen or methyl,
- $R^8$ represents hydrogen, straight-chain or branched $C_1-C_3$-alkyl or cyclopropyl,
- $R^9$ represents hydrogen or methyl,
- $R^5$ represents hydrogen or methyl,
- $R^6$ represents hydrogen, and
- B represents $-CH_2-$, O or a direct bond, and their pharmaceutically utilizable hydrates and acid addition salts, as well as their alkali metal salts, alkaline earth metal salts, silver salts and guanidinium salts.

Particularly preferred compounds of the formula (I) are those in which
- $R^1$ represents hydrogen or methyl,
- $R^2$ hydrogen,
- $R^3$ represents methyl or ethyl,
- $R^{3'}$ represents hydrogen or methyl,
- $R^4$ represents hydrogen, methyl or ethyl,
- $X^1$ represents fluorine, Z represents radicals of the structures

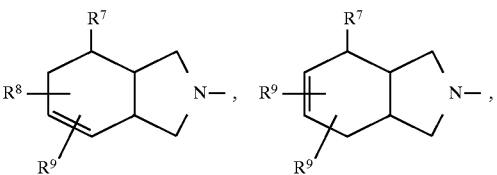

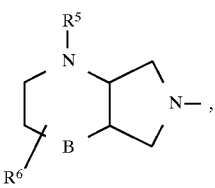

in which
- $R^7$ represents hydrogen, hydroxyl, $-NR^{10}R^{11}$, hydroxymethyl or $-CH_2-NR^{10}R^{11}$,
  where
  - $R^{10}$ represents hydrogen, methyl, alkoxycarbonyl having 1 to 4 C atoms in the alkoxy moiety or $C_1-C_3$-acyl,
  - $R^{11}$ represents hydrogen or methyl,
- $R^8$ represents hydrogen, straight-chain or branched $C_1-C_3$-alkyl or cyclopropyl,
- $R^6$ represents hydrogen,
- $R^9$ represents hydrogen or methyl,
- $R^5$ represents hydrogen or methyl, and
- B represents $-CH_2-$, O or a direct bond, and their pharmaceutically utilizable hydrates and acid addition salts, as well as their alkali metal salts, alkaline earth metal salts, silver salts and guanidinium salts.

The following compounds of the formula (I) may be mentioned specifically:

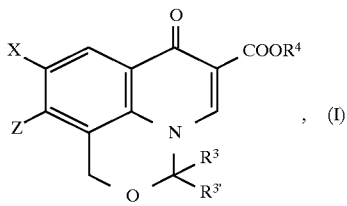

| $R^{3'}$ | $R^3$ | $R^4$ | Z | X |
|---|---|---|---|---|
| H | Me | H | | F |
| H | Me | H | ![structure](CH3-N-morpholine-pyrrolidine with O) | F |

-continued
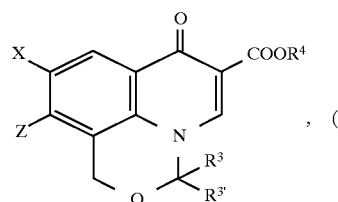
| R³' | R³ | R⁴ | Z | X |
|---|---|---|---|---|
| H | Me | H | 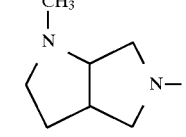 | F |
| H | Me | Et | 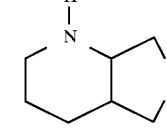 | F |
| H | Et | H | 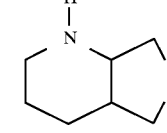 | F |
| Me | Me | H | 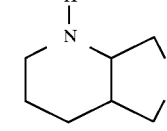 | F |
| Me | Me | H | 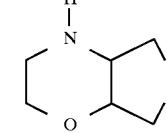 | F |
| CH₂OH | Me | H | 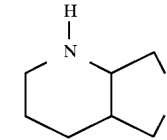 | F |
| H | H | H | 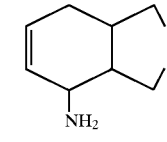 | F |
| H | H | ethyl | 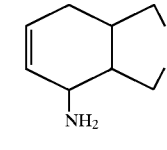 | F |
| H | H | H | 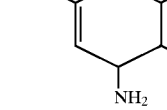 | F |

-continued
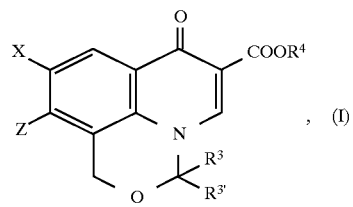
| R3' | R3 | R4 | Z | X |
|---|---|---|---|---|
| H | H | H | 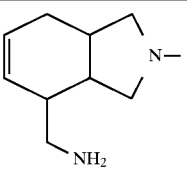 | F |
| CH₃ | H | ethyl | 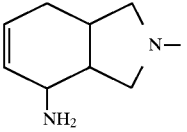 | F |
| H | H | —CH₂—CH₂—NH₂ | 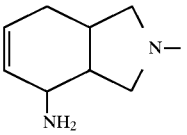 | F |
| H | H | —CH₂—CH₂—OCH₃ | 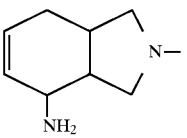 | F |
| CH₃ | H | H | 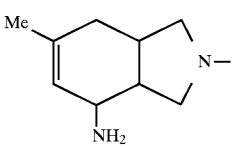 | F |
| CH₃ | CH₃ | H | 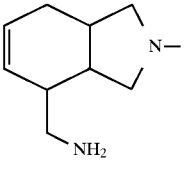 | F |
| H | CH₃ | ethyl | 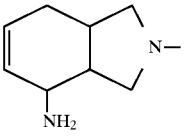 | F |
| H | CH₃ | —CH₂—CH₂—NH₂ | 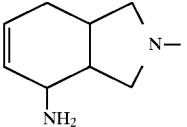 | F |
| H | CH₃ | —CH₂—CH₂—OCH₃ | 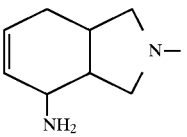 | F |

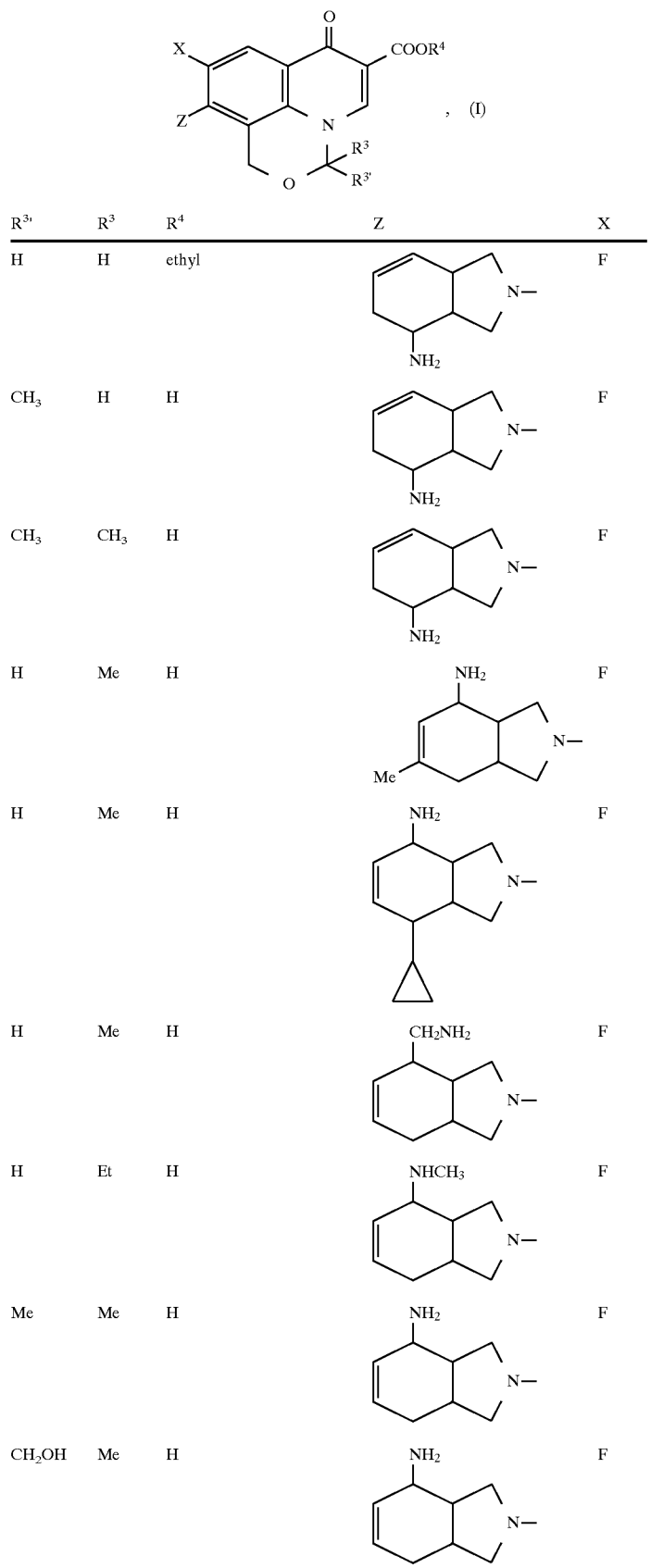

-continued

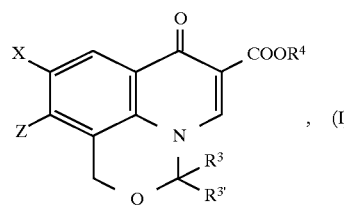, (I)

| R3' | R3 | R4 | Z | X |
|---|---|---|---|---|
| H | Me | H | NH2 (on bicyclic cyclohexene-pyrrolidine) | F |
| H | Me | H | NHCH3 (on bicyclic cyclohexene-pyrrolidine) | F |
| H | Me | H | NHC2H5 (on bicyclic cyclohexene-pyrrolidine) | F |
| H | Me | H | N(CH3)2 (on bicyclic cyclohexene-pyrrolidine) | F |
| H | Me | H | CH2NH2 (on bicyclic cyclohexene-pyrrolidine) | F |
| H | Me | H | CH2NHCH3 (on bicyclic cyclohexene-pyrrolidine) | F |
| H | Me | H | NH2, H3C substituent (on bicyclic cyclohexene-pyrrolidine) | F |
| H | Me | H | NH2, CH3 on ring (on bicyclic cyclohexene-pyrrolidine) | F |
| H | Me | H | NH2, CH3 on ring (on bicyclic cyclohexene-pyrrolidine) | F |

-continued
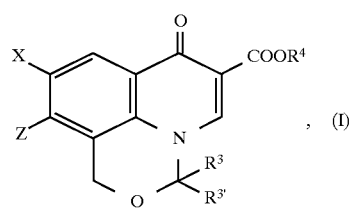, (I)
| R³' | R³ | R⁴ | Z | X |
|---|---|---|---|---|
| H | Me | H | NHCO₂Et-(bicyclic) | F |
| H | Me | H | (bicyclic) | F |
| H | Me | H | CH₂OH-(bicyclic) | F |
| H | Me | H | CH₂NHCO₂Et-(bicyclic) | F |
| Me | Me | H | NHCH₃-(bicyclic) | F |
| Me | Me | H | CH₂NH₂-(bicyclic) | F |
| CH₂OH | Me | H | NH₂-(bicyclic) | F |
| CH₂OH | Me | H | NHCH₃-(bicyclic) | F |
| CH₂OH | Me | H | CH₂NH₂-(bicyclic) | F |

-continued

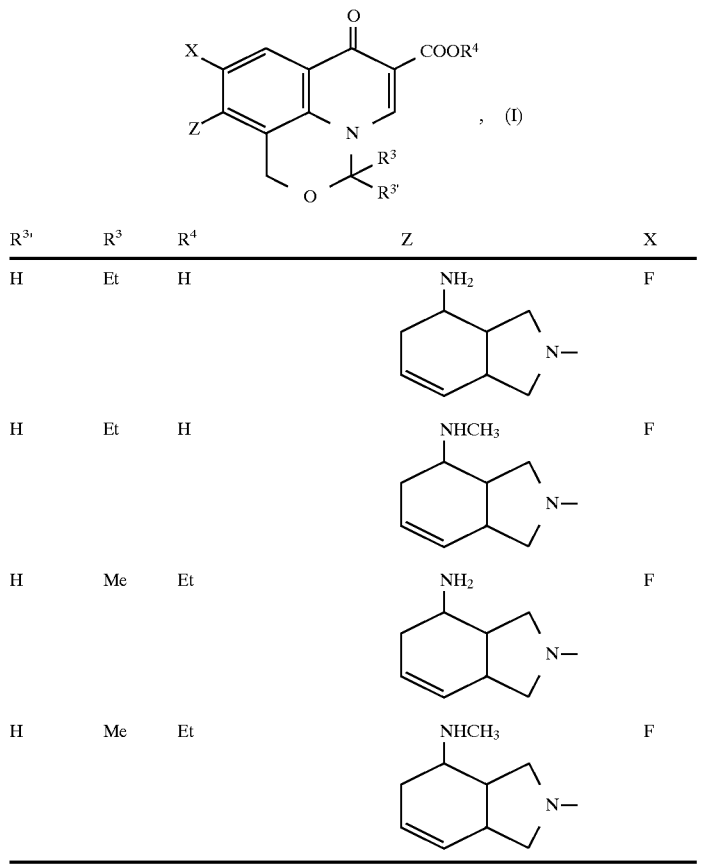

| R³' | R³ | R⁴ | Z | X |
|---|---|---|---|---|
| H | Et | H | NH₂ (cyclohexene-fused pyrrolidine) | F |
| H | Et | H | NHCH₃ (cyclohexene-fused pyrrolidine) | F |
| H | Me | Et | NH₂ (cyclohexene-fused pyrrolidine) | F |
| H | Me | Et | NHCH₃ (cyclohexene-fused pyrrolidine) | F |

If, for example, 9,10-difluoro-3-methyl-7-oxo-1H, 3H, 7H-pyrido[1,2,3-d,e]-[3,1]benzoxazine-6-carboxylic acid and 2,8-diazabicyclo[4.3.0]nonane are used for the preparation of compounds of the formula (I), the course of the reaction can be represented by the following equation:

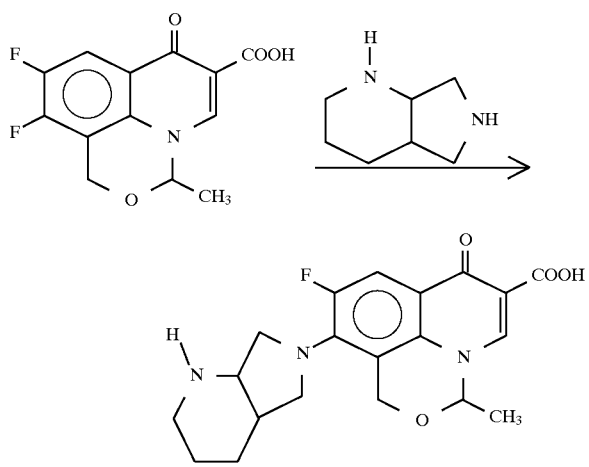

The compounds of the formula (II) which are used as starting compounds are known or can be prepared by known processes. If appropriate, they can be employed in the form of the racemates, enantiomers or pure diastereomers.

Examples which may be mentioned are:
9,10-difluoro-3-methyl-7-oxo- 1H,3H,7H-pyrido-[3,2,1-i,j][3,1]benzoxazine-6-carboxylic acid
9,10-difluoro-3-ethyl-7-oxo-1H,3H, 7H-pyrido-[3,2,1-i,j][3,1]benzoxazine-6-carboxylic acid
9,10-chloro-3-methyl-7-oxo-1H,3H,7H-pyrido-[3,2,1-i,j][3,1]benzoxazine-6-carboxylic acid
9,10-difluoro-3-dimethyl-7-oxo- 1H,3H,7H-pyrido-[3,2,1-i,j][3,1]benzoxazine-6-carboxylic acid
ethyl 9,10-difluoro-3-methyl-7-oxo- 1H,3H,7H-pyrido-[3,2,1-i,j][3,1]benzoxazine-6-carboxylate The amines of the formula (III) which are used as starting compounds are known. Chiral amines can be employed in the form of the racemates as well as enantiomerically or diastereomerically pure compounds.

Examples which may be mentioned are:
2,7-diazabicyclo[3.3.0]octane
2-methyl-2,7-diazabicyclo[3.3.0]octane
2,8-diazabicyclo[4.3.0]nonane
2-methyl-2,8-diazabicyclo[4.3.0]nonane
2-oxa-5,8-diazabicyclo[4.3.0]nonane
5-methyl-2-oxa-5,8-diazabicyclo[4.3.0]nonane
2-amino-8-azabicyclo[4.3.0]non-3-ene
2-methylamino-8-azabicyclo[4.3.0]non-3-ene
4-methyl-2-methylamino-8-azabicyclo[4.3.0]non-3-ene
5-methyl-2-methylamino-8-azabicyclo[4.3.0]non-3-ene
2-dimethylamino-8-azabicyclo[4.3.0]non-3-ene
2-ethylamino-8-azabicyclo [4.3.0]non-3-ene
2-methylaminomethyl-8-azabicyclo[4.3.0]non-3-ene
2-hydroxy-8-azabicyclo[4.3.0]non-3-ene
5-isopropyl-2-methylamino-8-azabicyclo[4.3.0]non-3-ene 2-amino-5-isopropyl-8-azabicyclo[4.3.0]non-3-ene
2-amino-5-methyl-8-azabicyclo[4.3.0]non-3-ene
2-hydroxymethyl-8-azabicyclo[4.3.0]non-3-ene
2-amino-5-cyclopropyl-8-azabicyclo[4.3.0]non-3-ene
8-azabicyclo[4.3.0]non-2-ene
ethyl 8-azabicyclo[4.3.0]non-4-ene-2-carboxylate
2-hydroxymethyl-8-azabicyclo[4.3.0]non-4-ene
2-amino-8-azabicyclo[4.3.0]non-4-ene
2-ethyl oxycarbonylamio-8-azabicyclo[4.3.0]on-4-ene
2-tert-butyloxycarbonylamino-8-azabicyclo[4.3.0]non-4-ene
2-benzyloxycarbonylamino-8-azabicyclo[4.3.0]non-4-ene
2-allyloxycarbonylarninomethyl-8-azabicyclo[4.3.0]non-4-ene
2-aminomethyl-8-azabicyclo[4.3.0]non-4-ene
2-ethyloxycarbonylaminomethyl-8-azabicyclo[4.3.0]non-4-ene
2-tert-butyloxycarbonylaminomethyl-8-azabicycl[4.3.0]non-4-ene
2-methylamino-8-azabicyclo[4.3.0]non-4-ene
2-ethylamino-8-azabicyclo[4.3.0]non-4-ene
2-cyclopropylamino-8-azabicyclo[4.3.0]non-4-ene
2-dimethylamino-8-azabicyclo[4.3.0]non-4-ene
2-[(2-hydroxyethyl)-amino]-8-azabicyclo[4.3.0]non-4-ene
2-amino-1-methyl-8-azabicyclo[4.3.0]non-4-ene
2-amino-2-methyl-8-azabicyclo[4.3.0]non-4-ene
2-amino-3-methyl-8-azabicyclo[4.3.0]non-4-ene
2-ethyloxycarbonylamino-3-methyl-8-azabicyclo[4.3.0]non-4-ene
2-tert-butyl oxycarbonylamino-3-methyl-8-azabicyclo[4.3.0]non-4-ene
2-benzyloxycarbonylamino-3-methyl-8-azabicyclo[4.3.0]non-4-ene
2-allyloxycarbonylaminomethyl-3-methyl-8-azabicyclo[4.3.0]non-4-ene
2-amino-4-methyl-8-azabicyclo[4.3.0]non-4-ene
2-amino-5-methyl-8-azabicyclo[4.3.0]non-4-ene
2-amino-6-methyl-8-azabicyclo[4.3.0]non-4-ene
2-amino-7-methyl-8-azabicyclo[4.3.0]non-4-ene
2-amino-9-methyl-8-azabicyclo[4.3.0]non-4-ene The substituted 8-azabicyclo[4.3.0]non-4-enes and 8-azabicyclo[4.3.0]non-2-enes as well as their preparation are disclosed in DE-OS (German Published Specification) 4 230 804.

They are obtained by reacting suitable dienes with suitable dienophiles in a Diels-Alder reaction, which can be carried out intermolecularly or intramolecularly, and, if appropriate, subsequently carrying out further chemical reactions so as to construct the pyrrolidine ring, if appropriate, and to introduce substituents which are desired for their biological action and, as the last step, eliminating the protective group from the pyrrolidine nitrogen.

If the Diels-Alder reaction is carried out intramolecularly, compounds of the formula (1) or (2)

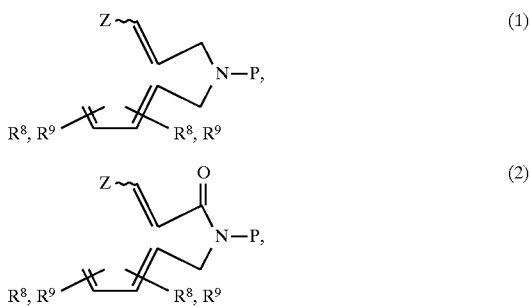

in which $R^8$ and $R^9$ have the abovementioned meaning and

P represents a protective group (for example allyl, acyl, carbamoyl or trityl), and Z represents hydrogen, a carboxyl, carboxylate or carboxamide group, CN or $NO_2$, are reacted to give compounds of the formula (3) [starting from (1)] or (4) [starting from (2)]

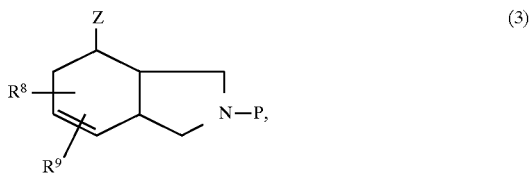

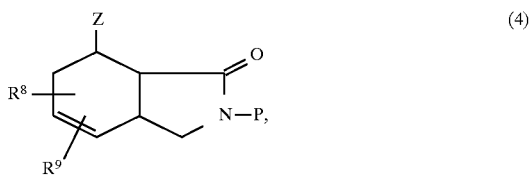

in which $R^8$, $R^9$, P and Z have the abovementioned meanings.

Some intramolecular Diels-Alder reactions of a similar type are known: J. M. Mellor, A. M. Wagland; J. Chem. Soc. Perkin I, 997–1005 (1989); W. R. Roush, S. E. Hall; J. Am. Chem. Soc. 103, 5200 (1980); E. Ciganek; Organic Reactions 32, 1–374 (1984). However, these publications fail to mention protective groups which are not only suitable for the reaction but can also be eliminated subsequently without problems.

If the Diels-Alder reaction is carried out intermolecularly, dienes of the formula (5) are reacted with dienophiles of the formula (6) to give compounds of the formula (7), and, if appropriate after modification of groups $Z^1$ and $Z^2$, for example conversion of a cyclic carboxylic anhydride into a diester with elimination of the protective groups $P^1$ or $P^1$ and $P^2$, subjected to a cyclization reaction to give the lactams of the formula (8).

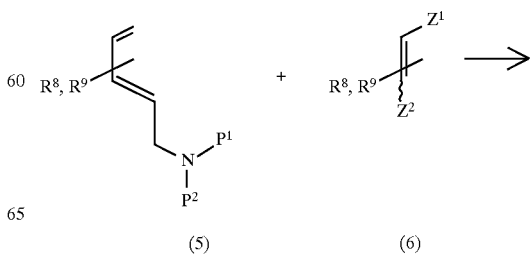

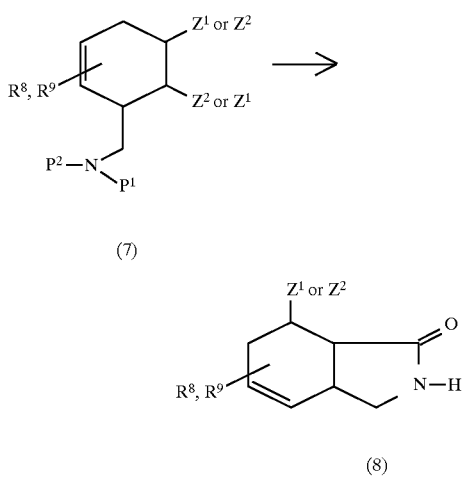

In formula (5), (6), (7) and (8), $R^8$ and $R^9$ have the abovementioned meaning, $P^1$ represents an acyl or carbamoyl protective group if $P^2$ represents hydrogen, or $P^1$ together with $P^2$ forms an imide, $Z^1$ and $Z^2$ represent hydrogen, carboxyl, carboxylate or carboxamide groups, CN or $NO_2$, where at least one of the two groups $Z^1$ or $Z^2$ must be a carboxylate group or a carboxamide group or CN, or $Z^1$ and $Z^2$ together form a bridge, so that a cyclic carboxylic anhydride is formed.

Preferred protective groups P, $P^1$ and $P^2$ are those protective groups in which, under the conditions used for their elimination, cyclization to the lactam and, if appropriate, an esterification of a second, as yet free carboxyl function with the alcohol used as the solvent takes place, in such a manner that all reaction steps can be carried out in a one-pot reaction and that uncontrolled conversion of starting substances, if appropriate diastereomerically and enantiomerically pure starting substances, into isomer mixtures which cannot be separated, or are difficult to separate, does not take place.

Examples which may be mentioned are:

1. the tert-butyloxycarbonyl protective group (eliminated using aqueous or alcoholic acids)
2. the phthalimido protective group (aminolysis using primary amines in aqueous or anhydrous alcohols as solvent)

The reaction of the compounds of the formula (II) with compounds of the formula (III), in which the compounds (III) may also be employed in the form of their salts, such as, for example, the hydrochlorides, is preferably carried out in a diluent such as dimethyl sulphoxide, N,N-dimethylformamide, N-methylpyrrolidone, hexamethylphosphoric triamide, sulpholane, acetonitrile, water, an alcohol such as methanol, ethanol, n-propanol, isopropanol, glycol monomethyl ether or pyridine. Mixtures of these diluents can also be used.

Acid binders which can be used are all customary inorganic and organic acid-binding agents. These preferably include the. alkali metal hydroxides, alkali metal carbonates, organic amines and amidines. Substances which may be mentioned specifically as being particularly suitable are: triethylamine, 1,4-diazabicyclo[2.2.2]octane (DABCO), 1,8-diazabicyclo[5.4.0]undec-7-ene (DBU) or excess amine (III).

The reaction temperatures can be varied within a substantial range. In general, the process is carried out between approximately 20° and 200° C., preferably between 80° and 180° C.

The reaction can be carried out under atmospheric pressure, but also under elevated pressure. In general, the process is carried out at pressures of between 1 bar and 100 bar, preferably between 1 and 10 bar.

When carrying out the process according to the invention, 1 to 15 mol, preferably 1 to 6 mol, of the compound (III) are employed per mole of the compound (II).

During the reaction, free amino groups may be protected by a suitable amino protective group, for example by the tert-butoxycarbonyl radical, and, after the reaction has ended, set free again by treatment with a suitable acid such as hydrochloric acid or trifluoroacetic acid (see Houben-Weyl, Methoden der Organischen Chemie [Methods in Organic Chemistry], Volume E4, page 144 (1983); J. F. W. Mc Omie, Protective Groups in Organic Chemistry (1973), page 43).

The esters according to the invention are obtained by reacting an alkali metal salt of the basic carboxylic acid which can optionally be protected on the N atom by a protective group, such as the tert-butoxycarbonyl radical, with suitable halogenoalkyl derivatives in a solvent such as dimethylformamide, dimethylacetamide, N-methylpyrrolidone, dimethyl sulphoxide or tetramethylurea, at temperatures from approximately 0° to 100° C., preferably 0° to 50° C.

The acid addition salts of the compounds according to the invention are prepared in the customary manner, for example by dissolving the betaine in a sufficient amount of aqueous acid and precipitating the salt with an organic solvent which is miscible with water, such as methanol, ethanol, acetone or acetonitrile. It is also possible to heat equivalent amounts of betaine and acid in water or an alcohol such as glycol monoethyl ether and subsequently evaporating the solution to dryness or filtering off with suction the salt which has precipitated. Pharmaceutically utilizable salts are to be understood as meaning, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. The compounds according to the invention may furthermore be bound to acidic or basic ion exchangers.

The alkali metal salts or alkaline earth metal salts of the carboxylic acids according to the invention are obtained, for example, by dissolving the betaine in a substoichiometric amount of alkali metal hydroxide solution or alkaline earth metal hydroxide solution, filtering off undissolved betaine and evaporating the filtrate to dryness. Pharmaceutically suitable are sodium salts, potassium salts or calcium salts. The corresponding silver salts are obtained by reacting an alkali metal salt or alkaline earth metal salt with a suitable silver salt, such as silver nitrate.

The compounds according to the invention have a powerful antibiotic action and combine low toxicity with a broad antibacterial spectrum against Gram-positive and Gram-negative microorganisms, in particular also against those which are resistant to various antibiotics such as, for example, penicillins, cephalosporins, aminoglycosides, sulphonamides and tetracyclins.

These valuable properties allow them to be used as chemotherapeutic action in medicine and veterinary medicine as well as substances for preserving inorganic and organic materials, in particular a wide range of organic materials, for example polymers, lubricants, paints, fibres, leather, paper and wood, foodstuffs and water.

The compounds according to the invention are active against a very broad spectrum of microorganisms. With their aid, Gram-negative and Gram-positive bacteria and bacteria-like microorganisms can be controlled, and the diseases caused by these pathogens can be prevented, alleviated and/or cured.

The compounds according to the invention are distinguished by an improved activity against dormant and resistant microorganisms. In the case of dormant bacteria, that is to say bacteria which show no detectable growth, the compounds are active at concentrations which are below those of similar substances. This not only refers to the amount to be employed, but also to the speed of destruction. Such results were observed in Gram-positive and -negative bacteria, in particular in Staphylococcus aureus, Micrococcus luteus and Enterococcus faecalis.

The compounds according to the invention also show surprising, increased activity against bacteria which are classified as less sensitive to comparable substances, in particular resistant Staphylococcus aureus and Enterococcus faecalis.

The compounds according to the invention are particularly active against bacteria and bacteria-like microorganisms. They are therefore particularly suitable for the prophylaxis and chemotherapy of local and systemic infections in human and veterinary medicine which are caused by these pathogens.

The compounds are furthermore suitable for controlling protozoonoses and helminthoses.

The compounds according to the invention can be used in various pharmaceutical preparations. Preferred pharmaceutical preparations which may be mentioned are tablets, coated tablets, capsules, pills, granules, suppositories, injectable solutions, suspensions and emulsions, solutions, suspensions and emulsions for oral administration, furthermore pastes, ointments, gels, creams, lotions, powders and sprays.

The minimum inhibitory concentrations (MICs) were determined by serial dilution methods using Iso-Sensitest agar (Oxoid). For each test substance, a series of agar plates was prepared whose active compound concentrations decreased as the dilution was doubled. The agar plates were inoculated using a multipoint inoculator (Denley). The cultures used for inoculation were overnight cultures of the pathogen which had previously been diluted to such an extent that each inoculation point contained approximately $10^4$ colony-forming units. The inoculated agar plates were incubated at 37° C., and the microbial growth was read off after approximately 20 hours. The MIC value (µg/ml) indicates the lowest active compound concentration at which no growth was observed with the naked eye.

The following table lists the MIC values of some of the compounds according to the invention in comparison with 9-fluoro-3-methyl-10-(4-methyl-1-piperazinyl)-7-oxo-1H,3H,7H-pyrido[3,2,1-i,j]-[3,1]-benzoxazine-6-carboxylic acid (EP-O 373 531) as reference compound.

TABLE

| | | MIC values | | | |
|---|---|---|---|---|---|
| | | Example No. | | | |
| Species | Strain | 1 | 4 | 5 | Reference |
| E. coli | Z 431 Lit | 0.015 | 0.06 | ≦0.015 | 0.05 |
| | 21 Bui | 4 | 4 | 4 | 0.05 |
| Klebsiella pneumoniae | 2363 Ge | 0.06 | 0.12 | 0.12 | 0.5 |
| Salmonella | 1 Fr | 0.06 | 0.25 | 0.12 | 1 |
| Enterobacter | 0,4 Ge 02-33 | 0.25 | 0.12 | 0.12 | 1 |

TABLE-continued

| | | MIC values | | | |
|---|---|---|---|---|---|
| | | Example No. | | | |
| Species | Strain | 1 | 4 | 5 | Reference |
| Staphylococcus aureus | Z 2 Lit | 0.12 | 0.5 | 0.12 | 16 |
| | 3781 Ge | 0.12 | 8 | 0.12 | 128 |
| Pseudomonas | BS 698 TGD | 4 | 8 | 16 | 64 |

EXAMPLE 1

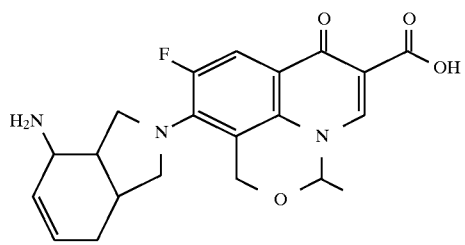

10-(2-Amino-8-azabicyclo[4,3,0]non-3-en-8-yl)-9-fluoro-3-methyl-7-oxo-1H,3H,7H-pyrido-[3,2,1-i,j][3,1]benzoxazine6-carboxylic acid 293 mg (1.04 mmol) of 9,10-difluoro-3-methyl-7-oxo-1H,3H,7H-pyrrido-[3,2,1-i,j][3,1]benzoxazine-6-carboxylic acid together with 200 mg (1.30 mmol) of 2-amino-8-azabicyclo[4,3,0]non-3-ene and 156 mg (1.4 mmol) of 1,4-diazabicyclo-[2,2,2]octane are heated in 1.5 ml of dimethyl sulphoxide for 60 minutes at 130° C. under argon. After cooling, the mixture is poured into water, the pH is brought to 7.5 using dilute hydrochloric acid, and the product is filtered off with suction. It is washed with water and dried in the air. For purification, the product is recrystallized from ethanol.

Yield: 150 mg (36% of theory)

Melting point: 207° C. (decomposition)

Diastereomer mixture

The following are obtained analogously:

EXAMPLE 2

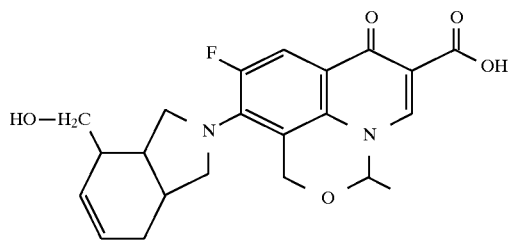

10-(2-Hydroxymethyl-8-azabicyclo[4,3,0]non-3-en-8-yl)-9-fluoro-3-methyl-7-oxo-1H,3H,7H-pyrido-[3,2,1-i,j][3,1]benzoxazine-6-carboxylic acid Melting point: 230° C. (decomposition)

Diastereomer mixture

EXAMPLE 3

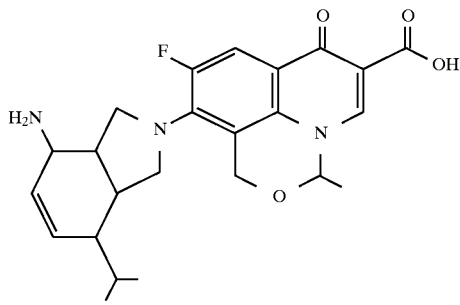

10-(2-Amino-5-isopropyl-8-azabicyclo[4,3,0]non-3-en-8-yl)-9-fluoro-3-methyl-7-oxo-1H,3H,7H-pyrido-[3,2,1-i,j][3,1]benzoxazine-6-carboxylic acid Melting point: 150° C. (decomposition)

Diastereomer mixture

EXAMPLE 4

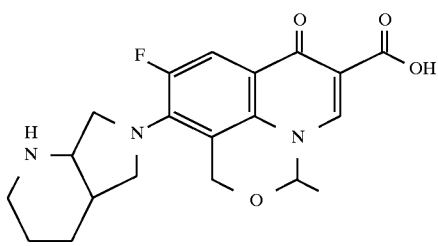

10-(2.8-Diazabicyclo[4,3,0]nonan-8-yl)-9-fluoro-3-methyl-7-oxo-1H,3H,7H-pyrido-[3,2,1-i,j][3,1]benzoxazine-6-carboxylic acid Melting point: 185° C. (decomposition)

Diastereomer mixture

EXAMPLE 5

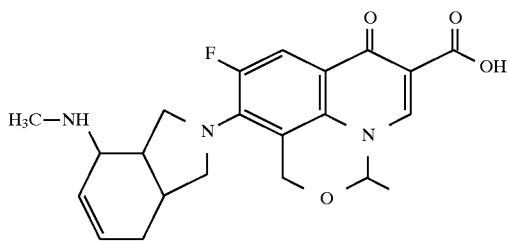

9-Fluoro-3-methyl-10-(2-methylamino-8-azabicyclo[4.3.0]non-3-en-8-yl)-7-oxo-1H,3H,7H-pyrido [3,2,1-i,j][3,]benzoxazine-6-carboxylic acid Melting point: 200° C. (decomposition)

Diastereomer mixture

EXAMPLE 6

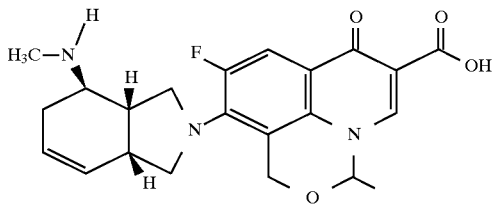

9-Fluoro-3 -methyl- 10-(2-methylamino-8-azabicyclo[4.3.0]non-4-en-8yl)-7-oxo-1H,3H,7H-pyrido[3.2.1-i,j][3.1]benzoxacine-6-carboxylic acid Melting point: 290° C. (decomposition)

Diastereomer mixture.

Preparation of the intermediates:

Example A:

8-Azabicyclo[4.3.0]non-2-ene

A.1. (E)-1-Bromo-2,4-pentadiene

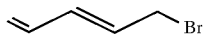

At 0° C., introduce 84 g (1.0 mol) of 1,4-pentadien-3-ol. Add dropwise with stirring 150 ml (≈1.3 mol) of 48% strength aqueous hydrobromic acid in such a manner that the internal temperature does not rise above 5° C. When the addition is complete, continue stirring for 1 h at room temperature. The organic phase is separated off and reacted further without purification.

Yield: 107–129 g (73–88% of theory)

A.2. (E)-1-(2-Propenylamino)-2,4-pentadiene

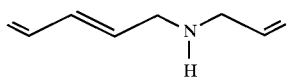

Introduce 228 g (4.0 mol) of 1-amino-2-propene. Add dropwise with stirring 58.8 g (0.4 mol) of (E)-1-bromo-2,4-pentadiene (title compound of Example A.1.). Keep the internal temperature in a range of 20°–30° C. by means of cooling. Stir for 5 h at room temperature. Concentrate batch at 150 mbar. Add 20 g (0.5 mol) of sodium hydroxide, dissolved in 200 ml of water, extract the mixture twice using in each case 100 ml of methylene chloride, dry using sodium sulphate, add 0.1 g of 4-hydroxyanisole, concentrate and distil at 40 mbar. 10–20 ppm of 4-hydroxyanisole are added to stabilize the distillate.

Yield: 33–35 g (67–72% of theory)

Boiling point: 77°–82° C. at 40 mbar $^1$H NMR (CDCl$_3$): δ=6.07–6.48 (m, 2H); 5.64–6.07 (m, 2H); 5.00–5.27 (m, 411); 3.19–3.36 ppm (m, 4H).

A.3. N-[(E)-2,4-Pentadienyl]-N-(2-propenyl)-acetamide

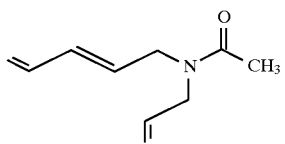

Introduce 24.6 g (0.2 mol) of (E)-1-(2-propenylamino)-2,4-pentadiene (title compound of Example A.2.), dropwise add 22.4 g of acetic anhydride, and stir overnight at room temperature. Concentrate and react further in the form of the crude product.

A.4. 8-Acetyl-8-azabicyclo[4.3.0]non-2-ene

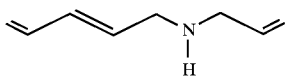

Dissolve 33.1 g (0.2 mol) of N-[(E)-2,4-pentadienyl]-N-(2-propenyl)-acetamide (title compound of Example A.3.) in 200 ml of xylene, pass through a vigorous stream of nitrogen for 15 min, add 0.1 g of 4-hydroxyanisole, then reflux overnight. Concentrate and distil under a high vacuum.

Yield: 23.1 g (70% of theory based on the title compound of Example A.2.)

Boiling point: 88°–93° C. at 0.05 mbar

A. 5.8-Azabicyclo[4.3.0]non-2-ene

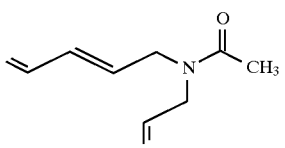

Reflux 16.5 g (0.1 mol) of 8-acetyl-8-azabicyclo[4.3.0]non-2-ene (title compound of Example A.4.) for 3 h in a mixture of 100 ml of 45% strength sodium hydroxide solution, 50 ml of water and 100 ml of 1,2-ethanediol. After cooling, extract four times using in each case 50 ml of diethyl ether. Dry combined organic phases using sodium sulphate and distil under a high vacuum.

Yield: 6.6 g (54% of theory)

Boiling point: 36°–44° C. at 0.35 mbar $^1$H NMR (CDCl$_3$): δ=5.79 (m, 1H); 5.74 (m, 1H); 3.02–3.17 (m, 2H); 2.47–2.72 (m, 2H); 2.06–2.30 (m, 2H); 1.91–2.06 (m, 2H); 1.68 (m, 1H); 1.45 ppm (m, 1H).

We claim:

1. A compound of the formula (I):

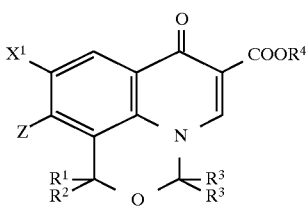

(I)

in which

R$^1$ represents hydrogen or C$_{1-4}$-alkyl which is optionally substituted by hydroxyl or halogen;

R$^2$ represents hydrogen or methyl;

R$^3$ represents hydrogen or C$_{1-4}$-alkyl;

R$^{3'}$ represents hydrogen or methyl;

R$^4$ represents hydrogen, C$_{1-4}$-alkyl which is optionally substituted by hydroxyl, methoxy, amino, methylamino or dimethylamino, or represents (5-methyl-2-oxo-1,3-dioxol-4-yl)methyl;

X$^1$ represents hydrogen or halogen;

Z represents a radical of the formula:

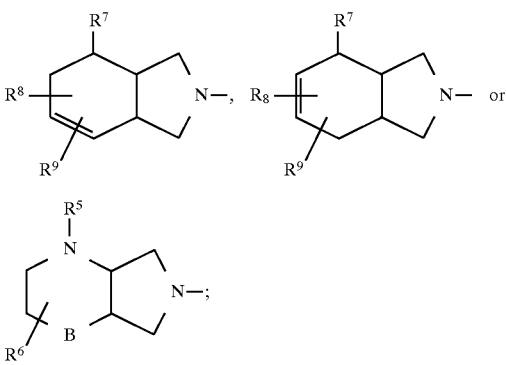

in which

R$^7$ represents hydrogen, hydroxyl, —NR$^{10}$R$^{11}$, hydroxymethyl, —CH$_2$—NR$^{10}$R$^{11}$, carboxyl, inethoxycarbonyl or ethoxycarbonyl;

in which

R$^{10}$ represents hydrogen, C$_{1-3}$-alkyl which is optionally substituted by hydroxyl, or represents C$_{1-4}$-alkoxycarbonyl or C$_{1-3}$-acyl- and R$^{11}$ represents hydrogen or methyl;

R$^8$ represents hydrogen, straight-chain or branched C$_{1-3}$-alkyl, or cyclopropyl;

R$^9$ represents hydrogen or methyl;

R$^6$ represents hydrogen or methyl;

R$^5$ represents hydrogen, methyl, —CH=CH—CO$_2$R$^{5'}$, —CH$_2$—CH$_2$—CO$_2$R$^{5'}$, —CH$_2$—CO—CH$_3$ or —CH$_2$—CH$_2$—CN;

in which

R$^{5'}$ represents methyl or ethyl;

B represents —CH$_2$—, —O— or a direct bond;

optionally in the form a racemic mixture or a pure enantiomer thereof, and/or of a pharmaceutically utilizable hydrate or acid addition salt, alkali metal salt, alkaline earth metal salt, silver salt or guanidinium salt thereof.

2. A compound of the formula (I) according to claim 1, in which

R$^1$ represents hydrogen or C$_1$–C$_3$-alkyl which is optionally substituted by hydroxyl, R$^2$ independently of R$^1$ represents hydrogen or methyl, R$^3$ represents hydrogen, methyl or ethyl, R$^{3'}$ represents hydrogen or methyl, R$^4$ represents hydrogen, alkyl having 1 to 4 carbon atoms which is optionally substituted by hydroxyl, methoxy, amino, methylamino or dimethylamino, or represents (5-methyl-2-oxo-1,3-dioxol-4-yl)methyl, X$^1$ represents hydrogen, fluorine or chlorine, Z represents radicals of the structures

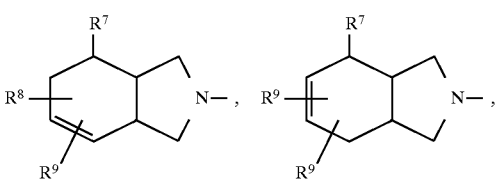

-continued

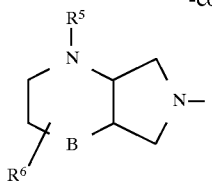

in which
R⁷ represents hydrogen, hydroxyl, —NR¹⁰R¹¹, hydroxymethyl or —CH₂—NR¹⁰R¹¹,
where
R¹⁰ represents hydrogen, C₁–C₂-alkyl which is optionally substituted by hydroxyl, or represents alkoxycarbonyl having 1 to 4 C atoms in the alkoxy moiety, or C₁–C₃-acyl,
R¹¹ represents hydrogen or methyl,
R⁸ represents hydrogen, straight-chain or branched C₁–C₃-alkyl or cyclopropyl,
R⁹ represents hydrogen or methyl,
R⁵ represents hydrogen or methyl,
R⁶ represents hydrogen, and
B represents —CH₂—, O or a direct bond.

3. A compound of the formula (I) according to claim 1, in which
R¹ represents hydrogen or methyl,
R² represents hydrogen,
R³ represents methyl or ethyl,
R³' represents hydrogen or methyl,
R⁴ represents hydrogen, methyl or ethyl,
X¹ represents fluorine,
Z represents radicals of the structures

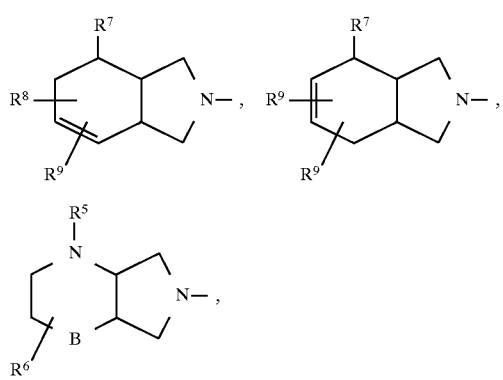

in which
R⁷ represents hydrogen, hydroxyl, —NR¹⁰R¹¹, hydroxymethyl or —CH₂—NR¹⁰R¹¹, where
R¹⁰ represents hydrogen, methyl, alkoxycarbonyl having 1 to 4 C atoms in the alkoxy moiety or C₁–C₃-acyl,
R¹¹ represents hydrogen or methyl,
R⁸ represents hydrogen, straight-chain or branched C₁–C₃-alkyl or cyclopropyl,
R⁶ represents hydrogen,
R⁹ represents hydrogen or methyl,
R⁵ represents hydrogen or methyl, and
B represents —CH₂—, O or a direct bond.

4. An antibacterial composition comprising a antibacterially effective amount of a compound of formula (I) according to claim 1 and a pharmaceutically acceptable carrier.

5. A method of preventing or combatting a bacterial infection in a patient comprising administering to said patient an antibacterially effective amount of a compound of formula (I) according to claim 1.

6. A process for preparing a compound of the formula (I) according to claim 1, said process comprising reacting a compound of the formula (II):

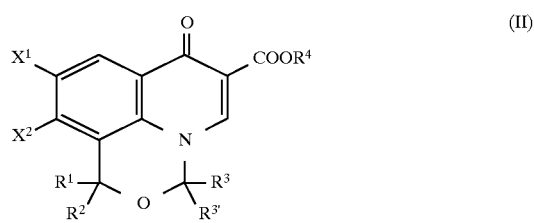

in which
R¹, R², R³, R³', R⁴ and X¹ have the ineaning given in claim 10; and
X² represents halogen;
with a compound of the formula (III):

in which
Z has the meaning given in claim 10;
optionally in the presence of an acid scavenger.

7. The process according to claim 6, wherein X² represents fluorine or chlorine.

* * * * *